(12) United States Patent
Yeh et al.

(10) Patent No.: US 6,465,492 B1
(45) Date of Patent: Oct. 15, 2002

(54) HETEROCYCLIC COMPOUNDS

(75) Inventors: Chun-Lin Yeh, Taichung (TW);
Chien-Hsing Chen, Taichung (TW)

(73) Assignee: Sinon Corporation, Taichung (TW)

( * ) Notice: Subject to any disclaimer, the term of this patent is extended or adjusted under 35 U.S.C. 154(b) by 0 days.

(21) Appl. No.: 09/833,331

(22) Filed: Apr. 12, 2001

(51) Int. Cl.[7] ............ A61K 31/44; C07D 413/00; C07D 417/00; C07D 401/00
(52) U.S. Cl. ............ 514/340; 514/341; 514/342; 546/271.4; 546/270.4; 546/272.4
(58) Field of Search ............... 514/342, 341, 514/340; 546/269.7, 271.4, 270.4, 272.7

(56) References Cited

PUBLICATIONS

Ca 123:55815, "Iminium carbonic acid derivative salts. VII. Part I: Electrophilic reactions of 2–methylthio–5, 6–dihydro–4H–1, 3–thiazinium iodides, 2–methylthio–4, 5–dihydrothizolium iodides, and 2–methylthio–5–methylthiazolium iodides with N–nucleophiles" cont. pp. 917–918, vol. 123, 1995.*

* cited by examiner

Primary Examiner—Alan L. Rotman
Assistant Examiner—Binta Robinson
(74) Attorney, Agent, or Firm—Timothy J. Keefer; Wildman, Harrold, Allen & Dixon

(57) ABSTRACT

A heterocyclic compound has the following formula (I)

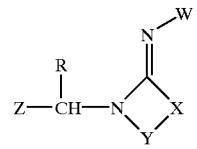

wherein Y represents a substituted or unsubstituted ethylene group or a trimethylene group, W represents the group —$SO_2R_1$, X represents an oxygen atom or sulfur atom or the group —$NR_2$ or —$CHR_3$, R represents a hydrogen atom or a methyl group and Z represents a pyridyl group.

13 Claims, No Drawings

HETEROCYCLIC COMPOUNDS

BACKGROUND OF THE INVENTION

1. Field of the Invention

This invention relates to heterocyclic compounds useful as pesticides.

2. Description of the Related Art

U.S. Pat. No. 4,742,060 discloses a heterocyclic compound of the formula

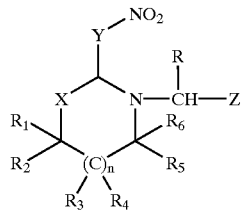

wherein n=0 or 1; X=S, O, —N—$R_7$ or —CH—$R_8$; Y=N or C—$R_9$; $R_7$, $R_8$, $R_9$=hydrogen or specific organic radicals; Z=5- or 6-membered nitrogen-containing heterocyclic ring; $R_1$, $R_2$, $R_5$, $R_6$=hydrogen or alkyl group; $R_3$, $R_4$=hydrogen, hydroxy group or alkyl group.

U.S. Pat. No. 4,849,432 discloses a heterocyclic compound that is similar to the aforementioned heterocyclic compound, except that the group —$NO_2$ is replaced by a —CN group and that Y is a nitrogen atom.

The above heterocyclic compounds are useful as pesticides.

The disclosures of the aforementioned U.S. patents are incorporated herein by reference in their entirety.

SUMMARY OF THE INVENTION

It is an object of the present invention to provide novel heterocyclic compounds that are useful as pesticides.

According to the present invention, a heterocyclic compound has the following formula (I):

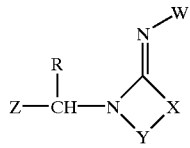

wherein Y represents a substituted or unsubstituted ethylene group or trimethylene group, W represents the group —$SO_2R_1$, in which $R_1$ represents a hydrogen atom, a $C_1$–$C_4$ alkyl group, a $C_1$–$C_4$ alkoxy group, a $C_2$–$C_4$ alkenyl group, or an aryl group, X represents an oxygen or sulfur atom or the group —$NR_2$ or —$CHR_3$, in which $R_2$ represents a hydrogen atom, a $C_1$–$C_4$ alkyl group, a $C_1$–$C_4$ alkoxy group, a $C_1$–$C_4$ alkylthio group, a $C_2$–$C_4$ alkenyl group, an alkylcarbonyl group, an alkylsulfonyl group, a pyridylmethyl group, a benzyl group, a formyl group, a phenylcarbonyl group, a phenoxycarbonyl group, or a phenylsulfonyl group, and in which $R_3$ represents a hydrogen atom or a $C_1$–$C_7$ alkyl group, R represents a hydrogen atom or a methyl group, and Z represents a pyridyl group optionally substituted by at least one substituent selected from agroup consisting of halogen atoms, $C_1$–$C_4$ alkyl groups, $C_2$–$C_4$ alkenyl groups, $C_1$–$C_4$ alkoxy groups, $C_1$–$C_4$ alkylcarbonyl groups, $C_1$–$C_4$ alkylthio groups, $C_1$–$C_4$ haloalkyl groups, $C_1$–$C_4$ haloalkoxy groups, $C_1$–$C_4$ alkylsulfonyl groups, a cyano group, and a nitro group.

DETAILED DESCRIPTION OF THE PREFERRED EMBODIMENTS

The present invention relates to a novel heterocyclic compound that has the following formula (I):

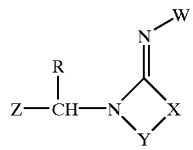

wherein Y represents a substituted or unsubstituted ethylene group or trimethylene group, W represents the group —$SO_2R_1$, in which $R_1$ represents a hydrogen atom, a $C_1$–$C_4$ alkyl group, a $C_1$–$C_4$ alkoxy group, a $C_2$–$C_4$ alkenyl group, or an aryl group, X represents an oxygen or sulfur atom or the group —$NR_2$ or —$CHR_3$, in which $R_2$ represents a hydrogen atom, a $C_1$–$C_4$ alkyl group, a $C_1$–$C_4$ alkoxy group, a $C_1$–$C_4$ alkylthio group, a $C_2$–$C_4$ alkenyl group, an alkylcarbonyl group, an alkylsulfonyl group, a pyridylmethyl group, a benzyl group, a formyl group, a phenylcarbonyl group, a phenoxycarbonyl group, or a phenylsulfonyl group, and in which $R_3$ represents a hydrogen atom or a $C_1$–$C_7$ alkyl group, R represents a hydrogen atom or a methyl group, and Z represents a pyridyl group optionally substituted by at least one substituent selected from a group consisting of halogen atoms, $C_1$–$C_4$ alkyl groups, $C_2$–$C_4$ alkenyl groups, $C_1$–$C_4$ alkoxy groups, $C_1$–$C_4$ alkylcarbonyl groups, $C_1$–$C_4$ alkylthio groups, $C_1$–$C_4$ haloalkyl groups, $C_1$–$C_4$ haloalkoxy groups, $C_1$–$C_4$ alkylsulfonyl groups, a cyano group, and a nitro group.

The heterocyclic compounds of formula (I) of this invention are found to be very effective against insects and are applicable for use in the agriculture industry.

The following Examples illustrate preparation of the heterocyclic compound of formula (I)

EXAMPLE 1

1.2 g of 2-[(4-methylphenyl)sulfonylimino] imidazolidine was dissolved in 30 ml of dry dimethylformamide. The mixture was subsequently added with 0.25 g of 60% sodium hydride at room temperature, and was stirred for 1 hour to form sodium salt of imidazolidine. The reaction mixture was added with 0.81 g of 6-chloro-3-chloromethylpyridine (CCMP) at room temperature, and was stirred for 3 hours. After the reaction, the remaining dimethylformamide was removed, and 15 ml of ice water and dichloromethane were added to the mixture. Dichloromethane was distilled off from the dichloromethane phase in the mixture to yield a yellowish solid. The yellowish solid was purified by known recrystallization techniques to yield 1.29 g white crystals of 3-(2-chloro-5-pyridylmethyl)-2-[(4-methylphenyl) sulfonylimino]imidazolidine. The thus formed crystals have a melting point in a range of from 178.5 to 179.2° C.

EXAMPLES 2–6

Example 1 was repeated, except that the reactant 2-[(4-methylphenyl)sulfonylimino]imidazolidine was replaced by an equivalent amount of 2-[(4-methylphenyl)sulfonylimino] tetrahydropyrimidine for Example 2, 2-[methylsulfonylimino]imidazolidine for Example 3, 2-[methylsulfonylimino]tetrahydropyrimidine for Example 4, 2-[(4-chlorophenyl)sulfonylimino]imidazolidine for Example 5, and 2-[(4-chlorophenyl)sulfonylimino] tetrahydropyrimidine for Example 6. The final products for the Examples 2 to 6 are respectively 3-(2-chloro-5-pyridylmethyl)-2-[(4-methylphenyl) sulfonylimino] tetrahydropyrimidine, 3-(2-chloro-5-pyridylmethyl)-2-[methylsulfonylimino] imidazolidine, 3-(2-chloro-5-pyridylmethyl)-2-[methylsulfonylimino] tetrahydropyrimidine, 3-(2-chloro-5-pyridylmethyl)-2-[(4-chlorophenyl)sulfonylimino]imidazolidine, and 3-(2-chloro-5-pyridylmethyl)-2-[(4-chlorophenyl)sulfonylimino] tetrahydropyrimidine.

EXAMPLE 7

A mixture of 1.62 g of 6-chloro-3-chloromethyl pyridine (CCMP), 2.56 g of 2-[(4-methylphenyl) sulfonylimino] thiazolidine, 3.0 g of potassium carbonate, and 50 ml acetonitrile was heated under reflux for 3 hours. After the reaction, the product in the reaction mixture was purified by known crystallization techniques to yield pale yellowish crystals of 3.51 g 3-(2-chloro-5-pyridylmethyl)-2-[(4-methylphenyl)sulfonylimino]thiazolidine. The thus formed crystals have a melting point in a range of from 162.1 to 162.8° C.

EXAMPLES 8 TO 12

Example 7 was repeated, except that the reactant 2-[(4-methylphenyl)sulfonylimino]thiazolidine employed in Example 7 was replaced by an equivalent amount of 2-[(4-methylphenyl)sulfonylimino]oxazolidine for Example 8, 2-[methylsulfonylimino]thiazolidine for Example 9, 2-[methylsulfonylimino]oxazolidine for Example 10, 2-[(4-chlorophenyl) sulfonylimino]thiazolidine for Example 11, and 2-[(4-chlorophenyl) sulfonylimino]oxazolidine for example 12. The final products for the Examples 8 to 12 were respectively 3-(2-chloro-5-pyridylmethyl)-2-[(4-methylphenyl)sulfonylimino]oxazolidine, 3-(2-chloro-5-pyridylmethyl)-2-[methylsulfonylimino]thiazolidine, 3-(2-chloro-5-pyridylmethyl)-2-[methylsulfonylimino] oxazolidine, 3-(2-chloro-5-pyridylmethyl)-2- [(4-chlorophenyl) sulfonylimino]thiazolidine, and 3-(2-chloro-5-pyridylmethyl)-2-[(4-chlorophenyl) sulfonylimino] oxazolidine.

Table 1 lists the formula and the melting point of the final product of each of the aforesaid Examples.

TABLE 1

| Example | formula | Melting point, ° C. |
|---|---|---|
| 1 | [structure with N—SO₂Tol] (Tol = Toluene) | 178.5–179.2 |
| 2 | [structure with SO₂Tol] | 155.2–156.0 |
| 3 | [structure with N—SO₂CH₃] | 130.2–130.9 |
| 4 | [structure with SO₂CH₃] | 153.9–154.6 |
| 5 | [structure with N—SO₂PhCl] (Ph = phenyl) | 178.3–179.7 |
| 6 | [structure with SO₂PhCl] | 151.7–152.5 |
| 7 | [structure with N—SO₂Tol, thiazolidine] | 162.1–162.8 |
| 8 | [structure with N—SO₂Tol, oxazolidine] | 153.5–154.2 |
| 9 | [structure with N—SO₂CH₃, thiazolidine] | 143.9–144.6 |
| 10 | [structure with N—SO₂CH₃, oxazolidine] | — |
| 11 | [structure with N—SO₂PhCl, thiazolidine] | 164.8–165.2 |

TABLE 1-continued

| Example | formula | Melting point, °C. |
|---------|---------|--------------------|
| 12 | 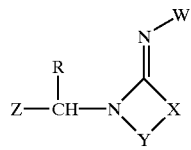 | 156.1–157.3 |

BIOLOGICAL TEST ON APHID

EXAMPLE 13

9.6 g of the compound (based on the active ingredient) obtained from Example 1 was blended with 90.4 g of a solvent to form a 9.6% w/w pesticide reagent An 8 cm×8 cm piece of cabbage leaf was placed on a lump of wetted cotton in each one of four Petri dishes. 20 aphids were subsequently put on the cabbage leaf in each one of the Petri dishes. The thus formed pesticide reagent was diluted 1000 times with water to form a diluted solution which was then sprayed onto the cabbage leaf in each one of the Petri dishes in a predetermined amount. The number of dead aphids in each one of the Petri dishes was examined after 24 hours.

EXAMPLES 14 TO 24

Example 13 was repeated, except that the compound employed in Example 13 was replaced by the compound obtained from a respective one of the Examples 2 to 12.

COMPARATIVE EXAMPLE 1

Example 13 was repeated, except that the compound employed in Example 13 was replaced by imidachloprid which is a heterocyclic compound of the formula disclosed in U.S. Pat. No. 4,742,060.

Table 2 lists the effectiveness of the pesticide reagents prepared in Examples 13 to 24 and the Comparative Example 1.

TABLE 2

| Example | Number of dead aphids | | | | | Effectiveness* |
|---------|-----|-----|-----|-----|---------|--------|
|         | 1st | 2nd | 3rd | 4th | average |        |
| blank   | 0   | 0   | 1   | 0   | 0.25    | —      |
| 13      | 15  | 18  | 16  | 17  | 16.5    | 82.28  |
| 14      | 16  | 17  | 17  | 16  | 16.5    | 82.28  |
| 15      | 16  | 18  | 19  | 19  | 18      | 89.87  |
| 16      | 17  | 17  | 19  | 19  | 18      | 89.87  |
| 17      | 20  | 18  | 19  | 20  | 19.25   | 96.20  |
| 18      | 19  | 19  | 19  | 17  | 18.5    | 92.41  |
| 19      | 17  | 16  | 18  | 17  | 17      | 84.81  |
| 20      | 17  | 16  | 18  | 15  | 16.5    | 82.28  |
| 21      | 16  | 18  | 19  | 18  | 17.75   | 88.61  |
| 22      | 18  | 16  | 19  | 17  | 17.5    | 87.34  |
| 23      | 18  | 18  | 16  | 18  | 17.5    | 87.34  |
| 24      | 15  | 18  | 19  | 19  | 17.75   | 88.61  |
| Comparative Example 1 | 18 | 17 | 18 | 16 | 17.25 | 86.08 |

*A higher value of effectiveness indicates greater effectivity for the pesticide reagent.

The above biological test results show that the heterocyclic compounds of formula (I) of this invention exhibit excellent pesticide function.

With the invention thus explained, it is apparent that various modifications and variations can be made departing from the spirit of the present invention. It is therefore intended that the invention be limited only as recited in the appended claims.

We claim:

1. A heterocyclic compound having the following formula (I):

$$Z-\underset{\underset{R}{|}}{CH}-N\underset{Y}{\overset{\displaystyle N-W}{\underset{\displaystyle \diagdown}{\diagup}}}X$$

wherein:

Y represents an ethylene group,

W represents the group —$SO_2R_1$, in which $R_1$ represents a hydrogen atom, a $C_1$–$C_4$ alkyl group, a $C_1$–$C_4$ alkoxy group, a $C_2$–$C_4$ alkenyl group, or an aryl group, X represents an oxygen or sulfur atom or the group —$NR_2$ or —$CHR_3$, in which $R_2$ represents a hydrogen atom, a $C_1$–$C_4$ alkyl group, a $C_1$–$C_4$ alkoxy group, a $C_1$–$C_4$ alkylthio group, a $C_2$–$C_4$ alkenyl group, an alkylcarbonyl group, an alkylsulfonyl group, a pyridylmethyl group, a benzyl group, a formyl group, a phenylcarbonyl group, a phenoxycarbonyl group, or a phenylsulfonyl group, and in which $R_3$ represents a hydrogen atom or a $C_1$–$C_7$ alkyl group, R represents a hydrogen atom or a methyl group, and Z represents a pyridyl group or a substituted pyridyl group wherein said-substituents are selected from the group consisting of halogen atoms, $C_1$–$C_4$ alkyl groups, $C_2$–$C_4$ alkenyl groups, $C_1$–$C_4$ alkoxy groups, $C_1$–$C_4$ alkylcarbonyl groups, $C_1$–$C_4$ alkylthio groups, $C_1$–$C_4$, haloalkyl groups, $C_1$–$C_4$ haloalkoxy groups, $C_1$–$C_4$ alkylsulfonyl groups, a cyano group, a nitro group, or mixtures thereof.

2. The heterocyclic compound of claim 1, wherein:

Y is an ethylene group,

W is the group —$SO_2CH_3$,

X is the group —NH,

R is a hydrogen atom, and

Z is a 2-chloro-5-pyridyl group.

3. The heterocyclic compound of claim 1, wherein:

Y is an ethylene group,

W is the group —$SO_2CH_3$,

X is an oxygen atom,

R is a hydrogen atom, and

Z is a 2-chloro-5-pyridyl group.

4. The heterocyclic compound of claim 1, wherein:

Y is an ethylene group,

W is the group —$SO_2\ CH_3$,

X is a sulfur atom,

R is a hydrogen atom, and

Z is a 2-chloro-5-pyridyl group.

5. The heterocyclic compound of claim 1, wherein:

Y is an ethylene group,

W is the group —$SO_2C_6H_4$—$CH_3$,

X is the group —NH,

R is a hydrogen atom, and

Z is a 2-chloro-5-pyridyl group.

6. The heterocyclic compound of claim 1, wherein

Y is an ethylene group,

W is the group —$SO_2C_6H_4$,—$CH_3$,

X is an oxygen atom,

R is a hydrogen atom, and

Z is a 2-chloro-5-pyridyl group.

7. The heterocyclic compound of claim 1, wherein

Y is an ethylene group,

W is the group —$SO_2C_6H_4$—$CH_3$,

X is a sulfur atom,

R is a hydrogen atom, and

Z is a 2-chloro-5-pyridyl group.

8. The heterocyclic compound of claim 1, wherein:

Y is an ethylene group,

W is the group —$SO_2C_6H_4$—Cl,

X is the group —NH,

R is a hydrogen atom, and

Z is a 2-chloro-5-pyridyl group.

9. The heterocyclic compound of claim 1, wherein:

Y is an ethylene group,

W is the group —$SO_2C_6H_4$—Cl,

X is an oxygen atom,

R is a hydrogen atom, and

Z is a 2-chloro-5-pyridyl group.

10. The heterocyclic compound of claim 1, wherein

Y is an ethylene group,

W is the group —$SO_2C_6H_4$—Cl,

X is a sulfur atom,

R is a hydrogen atom, and

Z is a 2-chloro-5-pyridyl group.

11. A pesticide reagent comprising an effective amount of the heterocyclic compound of claim 1.

12. The pesticide reagent of claim 11 which further comprises a solvent blended with an effective amount of the heterocyclic compound of claim 1.

13. A method for killing insects comprising treating plant matter with an effective amount of the heterocyclic compound of claim 1.

* * * * *